(12) United States Patent
Sterzer et al.

(10) Patent No.: US 6,847,848 B2
(45) Date of Patent: Jan. 25, 2005

(54) INFLATABLE BALLOON CATHETER STRUCTURAL DESIGNS AND METHODS FOR TREATING DISEASED TISSUE OF A PATIENT

(75) Inventors: Fred Sterzer, Lawrence Township, Mercer County, NJ (US); Daniel D. Mawhinney, Livingston, NJ (US)

(73) Assignee: MMTC, INC, Princeton, NJ (US)

( * ) Notice: Subject to any disclaimer, the term of this patent is extended or adjusted under 35 U.S.C. 154(b) by 46 days.

(21) Appl. No.: 10/337,159

(22) Filed: Jan. 7, 2003

(65) Prior Publication Data

US 2004/0133254 A1 Jul. 8, 2004

(51) Int. Cl.⁷ .................................................. A61F 2/00
(52) U.S. Cl. ........................................ 607/101; 607/99
(58) Field of Search ......................... 606/27–31, 41–50; 607/96, 98–102, 105, 113

(56) References Cited

U.S. PATENT DOCUMENTS

| | | | | |
|---|---|---|---|---|
| 4,375,220 A | * | 3/1983 | Matvias ..................... | 607/102 |
| 5,007,437 A | * | 4/1991 | Sterzer ...................... | 607/138 |
| 5,061,267 A | * | 10/1991 | Zeiher ......................... | 606/40 |
| 5,344,435 A | * | 9/1994 | Turner et al. ............... | 607/101 |
| 5,498,251 A | * | 3/1996 | Dalton ........................ | 604/523 |
| 5,545,195 A | * | 8/1996 | Lennox et al. ............. | 607/105 |
| 5,974,343 A | * | 10/1999 | Brevard et al. ............. | 607/102 |
| 5,992,419 A | * | 11/1999 | Sterzer et al. ............. | 128/898 |
| 6,123,083 A | * | 9/2000 | McGrath et al. ........... | 128/898 |
| 6,230,060 B1 | * | 5/2001 | Mawhinney ................ | 607/101 |
| 6,312,428 B1 | * | 11/2001 | Eggers et al. .............. | 606/41 |
| 6,325,796 B1 | * | 12/2001 | Berube et al. .............. | 606/33 |

* cited by examiner

Primary Examiner—Roy D. Gibson
(74) Attorney, Agent, or Firm—George Seligsohn

(57) ABSTRACT

Each of various modifications of an integrated-structure inflatable balloon catheter design includes a longitudinal structure having a sharply-pointed insertion needle at a distal end of the longitudinal structure and an inflatable balloon situated intermediate a proximate end and the distal end of the longitudinal structure which is attached to said longitudinal structure. With the inflatable balloon in a deflated state, the insertion needle may be used to puncture the patient's skin and underlying sub-cutaneous tissue and place the deflated balloon in proximity to the diseased sub-cutaneous tissue, The balloon is then inflated to press against and thereby spatially deform the diseased sub-cutaneous tissue, after which the deformed diseased sub-cutaneous tissue may be therapeutically heated. This heating may be sufficient to cause the creation of a permanent cavity in the deformed diseased sub-cutaneous tissue which persists after the catheter is withdrawn. This permits any selected one of various therapeutic substances to be introduced into this a permanent cavity. One modification employs a balloon having a selected non-uniform, odd pattern shape which, when inflated, cooperates with the shape of the diseased sub-cutaneous tissue. This one modification also may be beneficially used in prostate-treating balloon catheters, which do not have a sharply-pointed insertion needle at the distal end thereof.

31 Claims, 10 Drawing Sheets

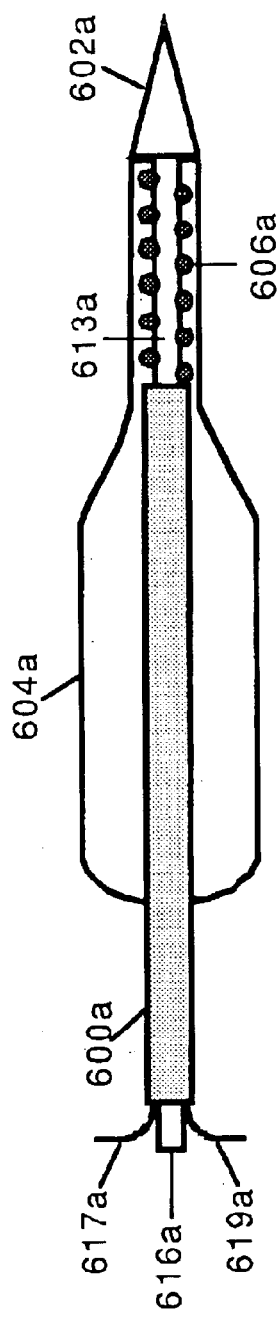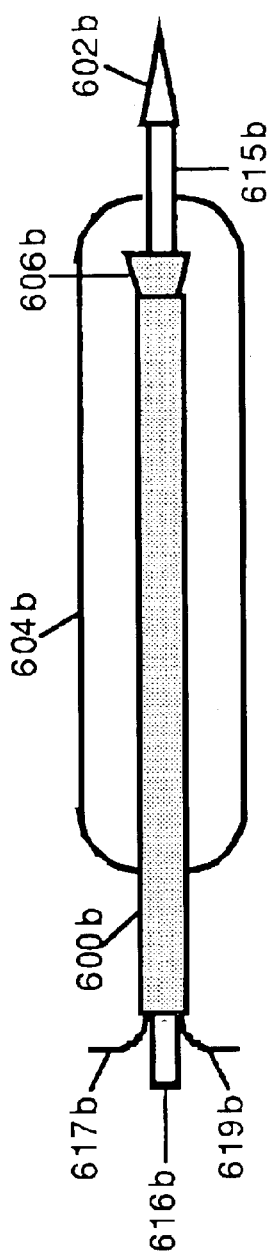
FIG. 6a
FIG. 6b

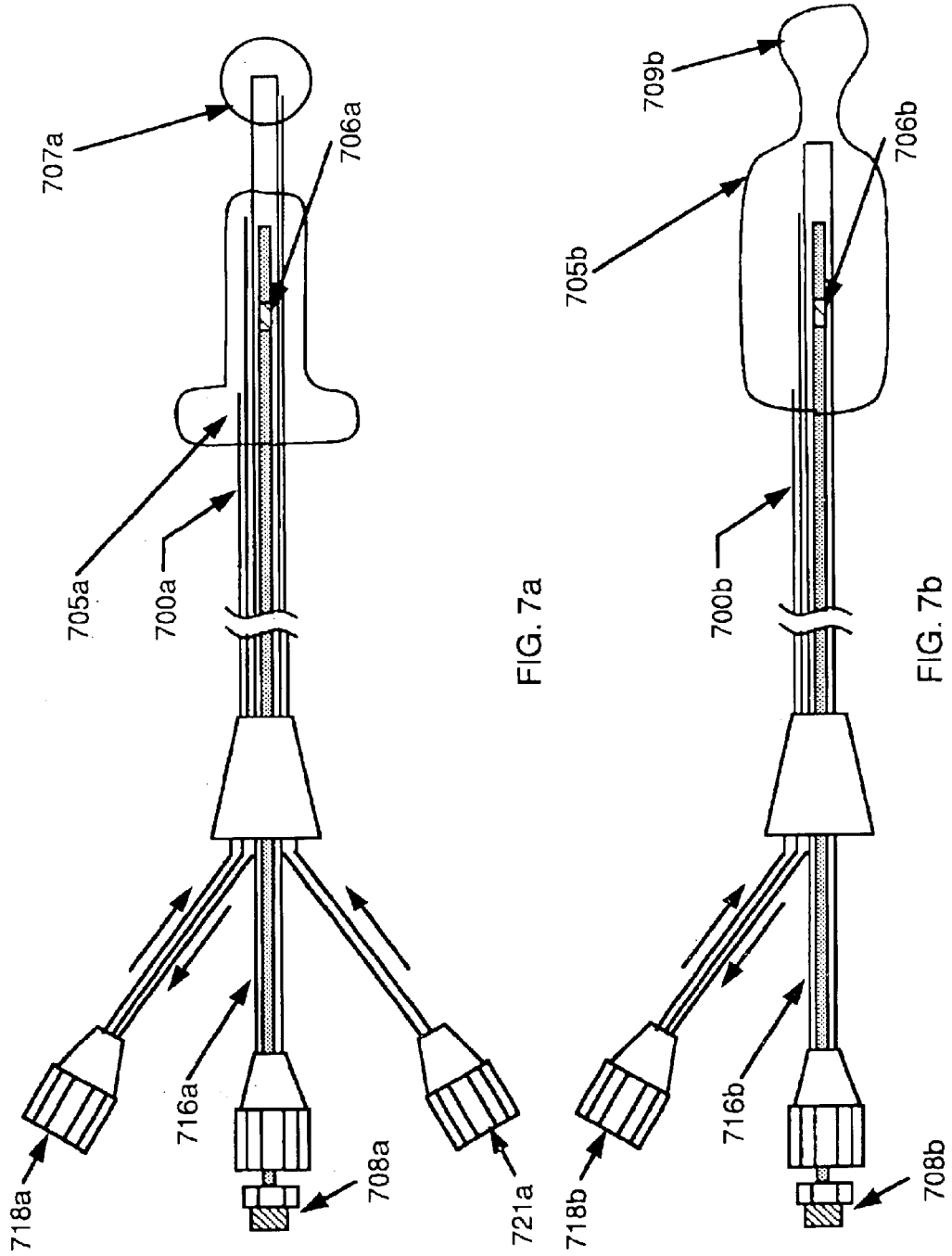

INFLATABLE BALLOON CATHETER STRUCTURAL DESIGNS AND METHODS FOR TREATING DISEASED TISSUE OF A PATIENT

BACKGROUND

1. Field of the Invention

This invention relates to various types of minimally-invasive inflatable balloon catheter designs and methods incorporating some type of means (e.g., a microwave-radiating antenna) for generating therapeutic heat in diseased tissue of a patient, and, more particularly, to catheter designs having an integrated structure that are capable of treating sub-cutaneous diseased tissue, such as (1) deep-seated tumors and (2) varicose veins.

2. Description of the Prior Art

Incorporated herein by reference is U.S. Pat. No. 5,007,437, entitled "Catheters for Treating Prostate Disease," which issued to Fred Sterzer on Apr. 16, 1991 and is assigned to the same assignee as the present application. Briefly, U.S. Pat. No. 5,007,437 discloses that applying squeezing pressure to a diseased prostate, by means of a urethral and/or rectal catheter incorporating an inflatable prostate balloon, to compress the prostate while it is being irradiated from a microwave antenna, increases the therapeutic temperature to which the prostate tissue more distal to the microwave antenna can be heated without heating any non-prostate tissue beyond a maximum safe temperature, and reduces the temperature differential between the heated more distal and more proximate prostate tissue from the microwave antenna.

Further, incorporated herein by reference is Chapter Four (pages 105–120) of the publication *New Frontiers in Medical Device Technology*, edited by Rosen et al. and published by John Wiley & Sons, Inc. in 1995. This Chapter Four, which is authored by Fred Sterzer and is entitled "Localized Heating of Deep-Seated Tissues Using Microwave Balloon Catheters," discloses, on pages 110 and 111, in vitro experiments which show that simultaneous ballooning and microwave heating to a 45° C. of an animal vessel resulted in the vessel becoming stiff with a wide-open lumen, becoming, in effect, a "biological stent." Further, Chapter Four discloses, on page 117, that the temperatures produced inside the treated prostate can be non-invasively measured with a microwave radiometer and, on page 118, that with microwave balloon catheters it is possible to produce high therapeutic temperatures throughout the prostate gland without causing burning of tissues and to produce "biological stents" in the urethra in a single treatment session. In this regard, reference is made to U.S. Pat. No. 5,149,198, which issued to Sterzer on Sep. 22, 1992, and U.S. Pat. No. 5,688,050, which issued to Sterzer et al. on Nov. 18, 1997, which patents are directed to radiometers which may be used for measuring the temperature of a patient's body tissue. Finally, Chapter Four concludes, on pages 118 and 119, that potential applications for microwave balloon catheters include the production of "biological stents" in partially obstructed vessels or in the urethra.

Also, incorporated herein by reference is U.S. Pat. No. 5,992,419, entitled "Method Employing a Tissue-Heating Balloon Catheter to Produce a 'Biological Stent' in an Orifice or Vessel of a Patient's Body", which issued to Fred Sterzer et al. on Nov. 30, 1999, and is assigned to the same assignee as the present application. This method makes use of a tissue-heating balloon catheter for creating "biological stents" that permanently widen the bore of an orifice or vessel of a patient's body and, more particularly, to the preferred use of a microwave balloon catheter for permanently widening the bore of the urethra of a male patient suffering from a disease of the prostate (such as benign prostatic hypertrophy (BPH) or prostate cancer) which results in an enlarged prostate that causes the bore of the urethra be narrowed.

In addition, incorporated herein by reference is U.S. Pat. No. 6,230,060, entitled "Single Integrated Structural Unit for Catheter Incorporating a Microwave Antenna", which issued to Daniel D. Mawhinney on May 8, 2001, and is assigned to the same assignee as the present application. The tissue-heating balloon catheter designs disclosed is the aforesaid U.S. Pat. Nos. 5,007,437 and 5,992,419, involves the use of a urethral catheter with an inflatable balloon section to stretch the opening in the enlarged prostate and a radiating antenna section, that is spatially completely separate from and unconnected to the inflatable balloon section, to apply microwave energy to the stretched prostatic urethra with the objective, in the case of U.S. Pat. No. 5,992,419, of forming a long-lasting biological stent to relieve the symptoms of the affliction. The use of a separate antenna or applicator which must be inserted into the catheter forces several design compromises on both the catheter and the antenna, which are avoided in the case of the single integrated structural unit disclosed in U.S. Pat. No. 6,230,060.

Finally, the aforesaid Chapter Four of the publication *New Frontiers in Medical Device Technology*, on page 116, suggests the use of a catheter with a deflated balloon at its tip inserted into a large tumor volume to be heated by either radioactive seeds or a microwave antenna. Also, the News and Perspective article "Vanquishing Varicose Veins" appearing in *Health News/June* 2002 discloses a non-balloon catheter for use in applying either radio-frequency (RF) or laser energy in less-invasive treatments of varicose veins.

SUMMARY OF THE INVENTION

Minimally-invasive treatment of diseased sub-cutaneous tissue of a patient is provided by each of various modifications of an integrated-structure inflatable balloon catheter design that includes a longitudinal structure having a sharply-pointed insertion needle at a distal end of the longitudinal structure and an inflatable balloon situated intermediate a proximate end and the distal end of the longitudinal structure which is attached to said longitudinal structure. With the inflatable balloon in a deflated state, the insertion needle may be used to puncture the patient's skin and underlying sub-cutaneous tissue and place the deflated balloon in proximity to the diseased sub-cutaneous tissue, The balloon is then inflated to press against and thereby spatially deform the diseased sub-cutaneous tissue, after which the deformed diseased sub-cutaneous tissue may be therapeutically heated. This heating may be sufficient to cause the creation of a permanent cavity in the deformed diseased sub-cutaneous tissue which persists after the catheter is withdrawn. This permits any selected one of various therapeutic substances to be introduced into this a permanent cavity.

BRIEF DESCRIPTION OF THE DRAWING

FIGS. 6a and 6b, respectively, diagrammatically show first and second different inflatable balloon catheter designs for use in treating varicose veins; and FIGS. 7a and 7b, respectively, diagrammatically show first and second different inflatable balloon catheter designs for use in treating prostate disease.

DESCRIPTION OF THE PREFERRED EMBODIMENTS

Figure 1:
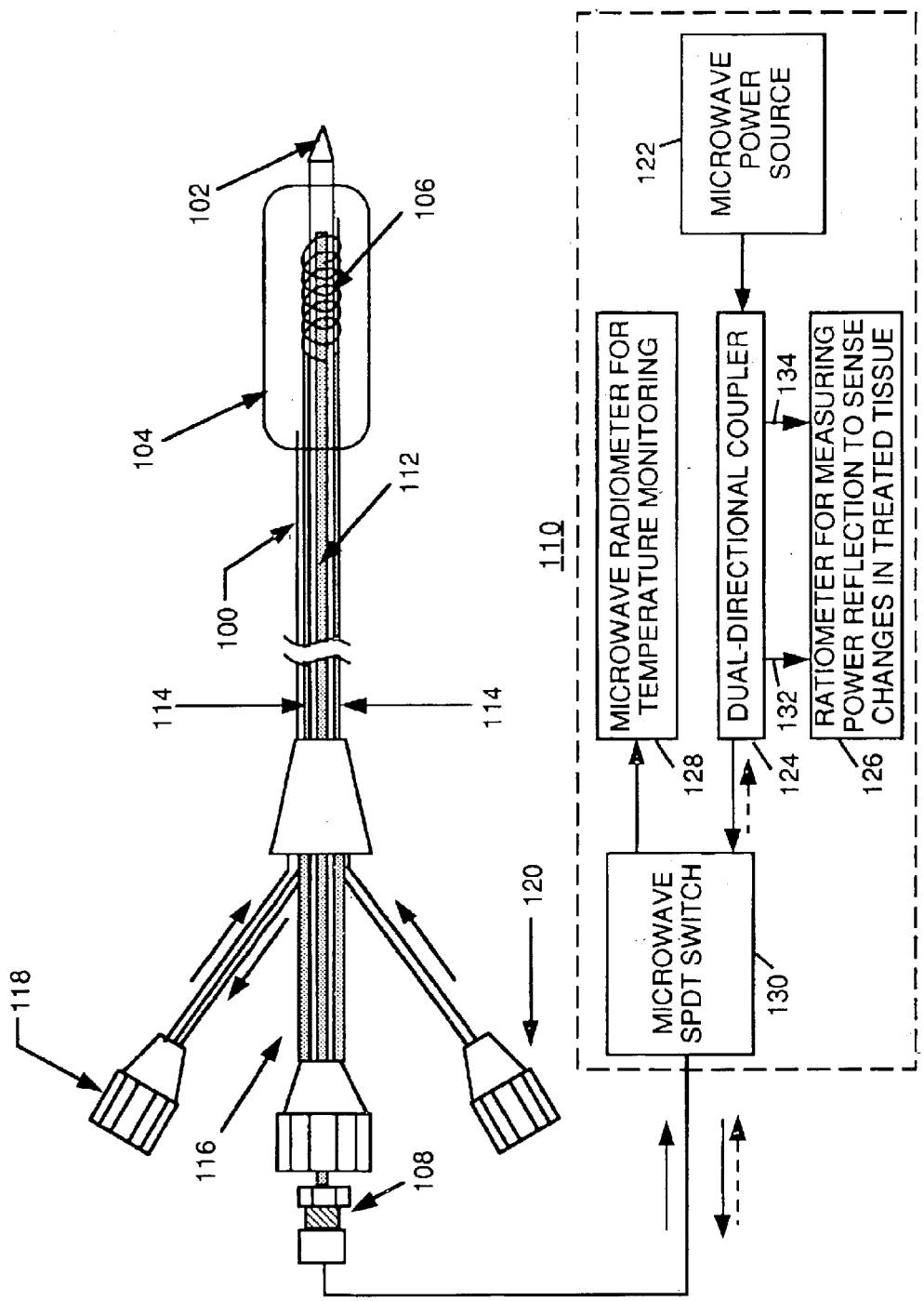
FIG. 1 is a generalized diagrammatic showing of an inflatable balloon catheter design of a type capable of treating sub-cutaneous tumors situated within deep-seated tissue along with operating circuitry associated therewith.

Referring to FIG. 1, there is shown a catheter design comprising integrated catheter body 100 terminating in sharp point 102 at its distal end. Further, toward its distal end, integrated catheter body 100 incorporates expansion balloon 104 and a radiating element in the form of maximum-diameter helical spring antenna 106. Toward its proximate end, integrated catheter body 100 comprises (1) connector 108 for use in transmitting microwave energy between microwave structure 110 and antenna 106 over hollow-interior inner conductor 112 and outer conductor 114 of coaxial feedline 116 to antenna 106, (2) connector 118 for use in providing a two-channel gas or liquid flow in the space between inner conductor 112 and outer conductor 114 to effect the inflation of expansion balloon 104, and (3) connector 120 for use in providing a two-channel liquid flow through the hollow interior inner conductor 112.

In operation, a relatively narrow-diameter (e.g., 2–10 mm) sharp point 102 of a relatively narrow-diameter (e.g., 2–10 mm) integrated catheter body 100, with expansion balloon 104 deflated, makes it possible to provide a minimally-invasive procedure for locating antenna 106 in or near a sub-cutaneous tumor situated within deep-seated tissue to be treated of a patient's body. During treatment, expansion balloon 104 is inflated to a relatively wide-diameter (e.g., 50–500 mm), after which the tumor may be irradiated with sufficient microwave energy to effect necrosis of tumor tissue and form a "biological stent" (as taught in the aforesaid prior-art U.S. Pat. No. 5,992,419). Expansion balloon 104 is then deflated and integrated catheter body 100 is removed from the patient's body.

Various examples of microwave structure suitable for use with a balloon-expansion catheter employing microwaves to heat diseased tissue of a patient are shown and described in detail in the aforesaid prior-art U.S. Pat. No. 5,992,419. The operation of microwave structure 110 makes use of the teachings of the aforesaid prior-art U.S. Pat. No. 5,992,419. In particular, microwave structure 110 comprises microwave power source 122, dual-directional coupler 124, ratiometer for measuring power reflection to sense changes in treated tissue 126, microwave radiometer for temperature monitoring 128 and microwave SPDT (single pole-double throw) switch 130. Although switch 130 may be a manually-operated switch, it is preferably an automated switch that periodically switches back and forth between first and second switch positions. In its first switch position, microwave energy from power source 122 is forwarded through dual-directional coupler 124 and switch 130 to antenna 106 of integrated catheter body 100 for irradiating the tumor tissue. This results in the tumor absorbing most of the microwave energy irradiating it, but a small amount of the microwave irradiating energy (having a quantitative value that depends on current characteristics of the tumor tissue being irradiated) is reflected back from the tumor tissue to antenna 106 and then returned through switch 130 (in its first switch position) to dual-directional coupler 124. A sample of this reflected-back microwave energy is applied as first input 132 to ratiometer for measuring power reflection to sense changes in treated tissue 126, while, at the same time, a sample of the microwave energy from power source 122 being forwarded to antenna 106 is applied as second input 134 to ratiometer for measuring power reflection to sense changes in treated tissue 126. In accordance with the teaching of the aforesaid prior-art U.S. Pat. No. 5,992,419, (1) block 126 includes circuitry for continuously determining the quantitative value of the ratio of the measured power values of the respective samples then being currently applied to inputs 132 and 134, and (2) an abrupt change in the quantitative value of this ratio is caused by a change in the characteristics of the irradiated tumor tissue that is indicative of the formation of a "biological stent". In the second switch position of switch 130, antenna 106 does not irradiate the tumor tissue with microwave energy, but, instead, antenna 106 receives microwave energy emitted by the tumor tissue having a frequency profile that depends on the current temperature of the emitting the tumor tissue. The microwave energy received by antenna 106 is returned through switch 130 in its second switch position to microwave radiometer for temperature monitoring 128. This permits microwave SPDT switch 130, periodically-operated between its first and second switch positions, to provide block 128 during each successive second position with a microwave frequency profile that is indicative of the current monitored temperature of the tumor tissue that is being heated during each successive first position. As taught in the aforesaid prior-art U.S. Pat. No. 5,992,419, the output from microwave radiometer 128, may be utilized, if desired, to automatically control the operation of microwave power source 122 to thereby control the rate of heating of the tumor tissue and/or to cutoff operation of microwave power source 122 in response to the irradiated tissue of the patient's body being heated to an unsafe temperature.

Figure 2A:
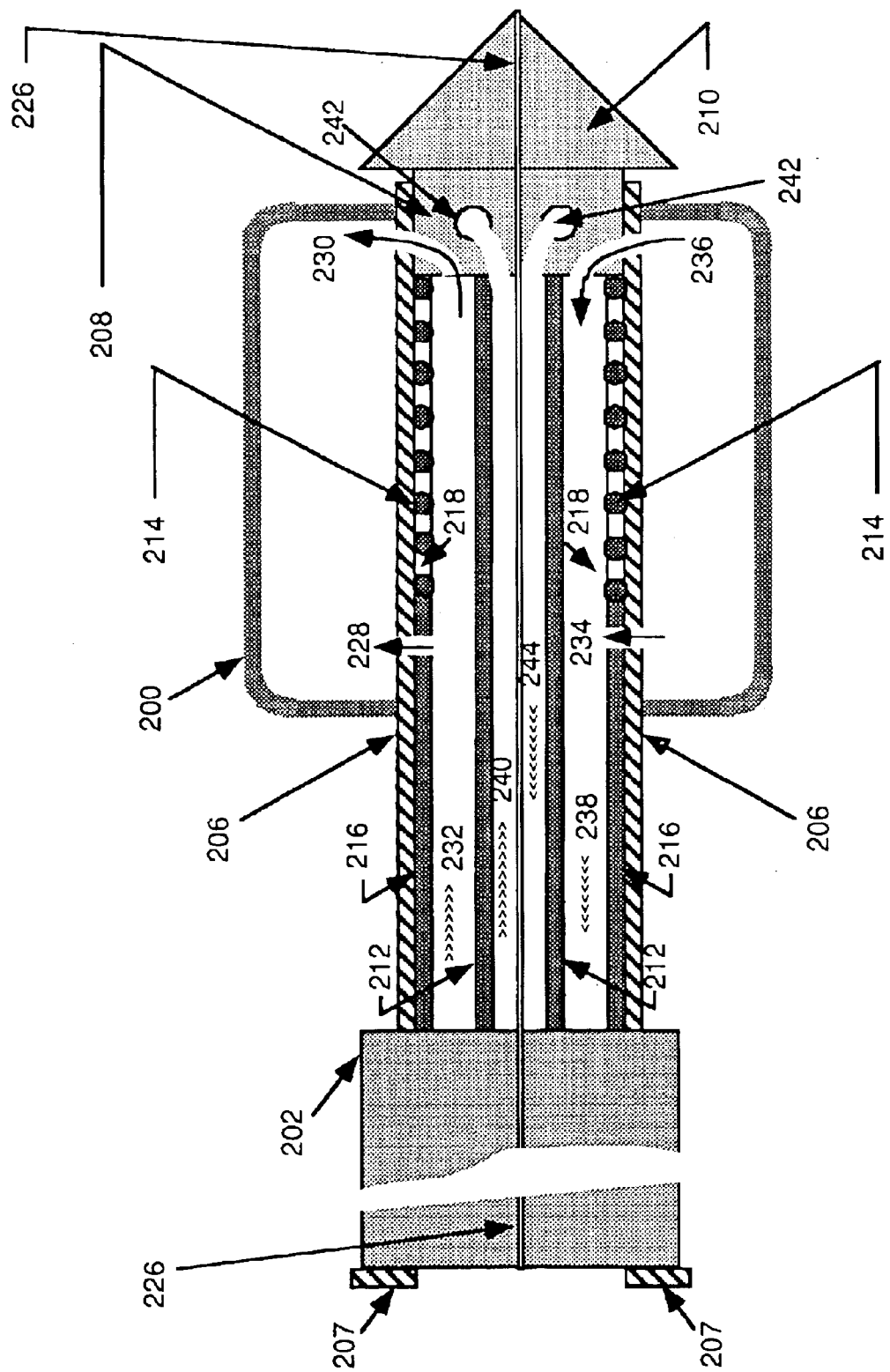
FIGS. 2a and 2b, respectively, are side and cross-sectional views of a preferred embodiment of an inflatable balloon catheter design capable of treating sub-cutaneous tumors situated within deep-seated tissue.
Figure 2B:
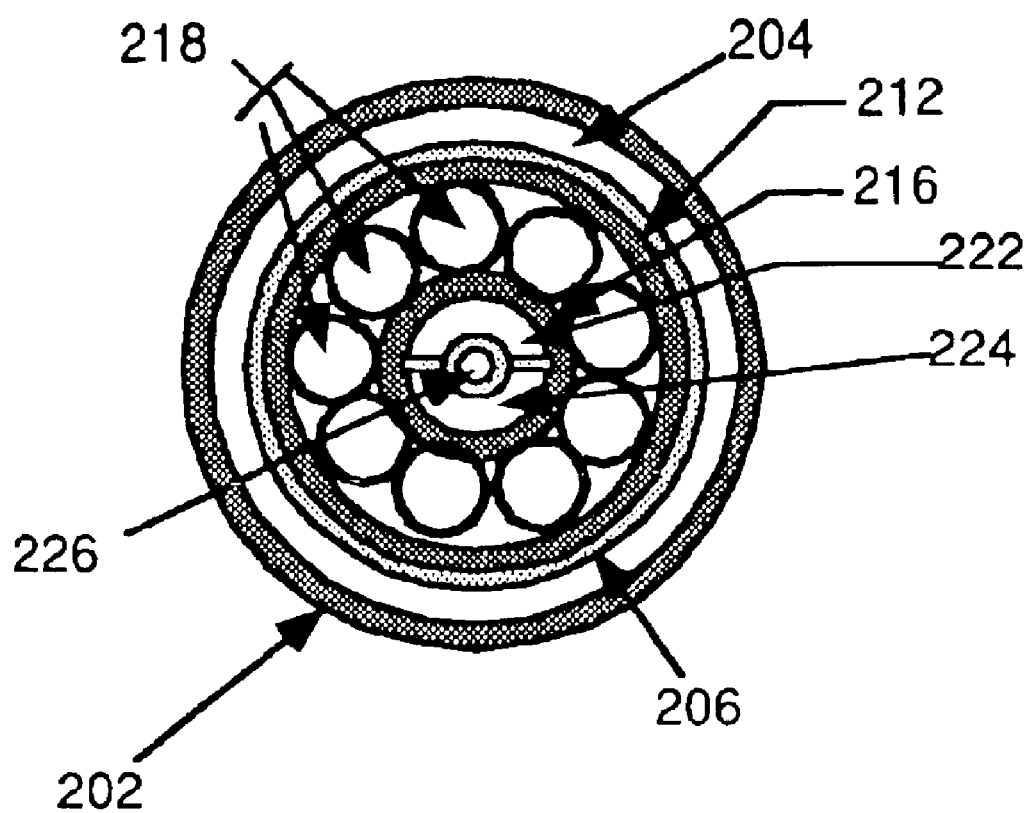

In the side view of the preferred integrated-structure catheter-design embodiment shown in FIG. 2a, inflatable balloon 200 is shown in its fully-expanded state and rigid (preferably metallic) retractable sheath 202 is shown in a retracted state. However, in the cross-sectional view of the preferred catheter-design embodiment shown in FIG. 2b, inflatable balloon 200 in a deflated and furled state is stored within space 204 situated between plastic catheter body 206 and retractable sheath 202 is assumed to be completely unretracted. More particularly, FIG. 2a shows (1) the proximate (i.e., left) end of plastic catheter body 206 terminating in tab 207 extending therefrom for preventing sheath 202 from being removed from of plastic catheter body 206 when sheath 202 has been fully retracted and (2) the interior surface of the distal end of plastic catheter body 206 attached to the proximate end of metal-block 208, with the distal end of metal-block 208 terminating in insertion needle 210. Balloon 200 is attached to the outer surface of plastic catheter body 206 toward the distal end thereof, as shown in FIG. 2a. A coaxial-cable feedline, which has its outer conductor 212 attached to the interior surface of plastic catheter body 206, extends the length of the catheter and has its distal end attached to the proximate end of helical spring antenna 214. Inner conductor 216, which is spaced from outer conductor 212 and supported by a contiguous plurality of circumferentially-arranged plastic tubes 218 situated in the space between outer conductor 212 and inner conductor 216 (FIG. 2b), extends the length of the catheter and has its distal end attached to the proximate end of metal-block 208 (FIG. 2a). While the length of helical spring antenna 214, which is in contact with the interior surface of plastic catheter body 206, is wound around and supported by the outer surface of plastic tubes 218, the distal end of helical antenna 214 is attached to the proximate end of metal-block 208. As indicated in FIG. 2a, helical spring antenna 214 is situated entirely within the volume of inflated balloon 200. As indicated in FIG. 2b, an element 220, which is attached to the interior surface of inner conductor 216 at each of two diametrically opposite points, runs the entire length of the catheter to thereby divide the interior space of inner conductor 216 into inlet channel 222 and outlet channel 224. Element 220 is shaped to define a central lumen 226 that extends the entire length of the catheter right through the tip of insertion needle 210 (FIG. 2a). A guide wire (not shown), used for directing and positioning the inserted catheter within the soft tissue of a patient being treated, may be passed through central lumen 226. In addition, central lumen 226 may be utilized, in a manner described below in more detail, to inject a liquid substance, such as an immunological stimulating drug, into a deep-seated tumor being treated.

While FIGS. 2a and 2b are not drawn to scale, the integrated-structure catheter-design embodiment shown therein may be implemented in a range of sizes. More specifically, the length of this integrated-structure catheter-design may range from 100 to 400 mm, with (1) retractable sheath 202 having an outer diameter ranging from 2 to 10 mm and an inner diameter ranging from 1.8 to 9 mm, (2) plastic catheter body 206 having an outer diameter ranging from 1.6 to 8 mm, (3) outer conductor 212 having an outer diameter ranging from 1.3 to 6.5 mm, (4) inner conductor 216 having an outer diameter ranging from 0.5 to 2.5 mm, and (5) central lumen 226 having a diameter ranging from 0.15 to 0.75 mm. Inflatable balloon 200 comprises plastic sheet material having a thickness that ranges from 0.2 to 1.0 mm. Inflatable balloon 200 has a length which ranges from 50 to 500 mm and has a width, when fully inflated, which ranges from 5 to 25 mm. The overall length of helical spring antenna 214 ranges from 40 to 400 mm, while the diameter of the wire of which helical spring antenna 214 is formed ranges from 0.3 to 2.0 mm. The number of the circumferentially-arranged plastic tubes 218 situated in the space between outer conductor 212 and inner conductor 216 ranges from 5 to 9 tubes, with each tube having a diameter which ranges from 0.8 to 4.0 mm.

Figure 3B:
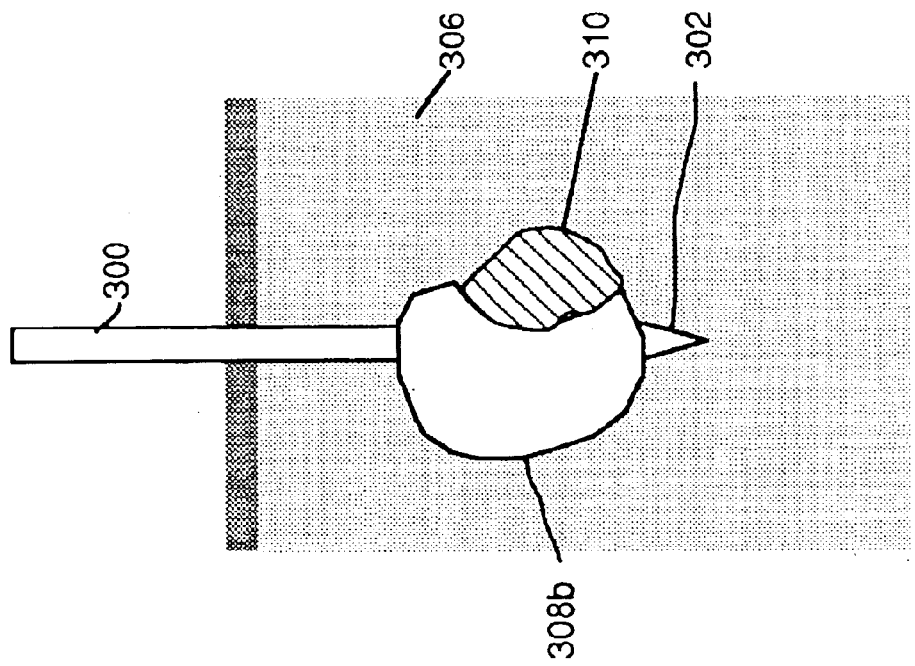
FIG. 3a schematically shows an inflatable balloon catheter that has been inserted through the skin of a patient and sub-cutaneous tissue with its balloon in its deflated state situated in proximity to a tumor within deep-seated tissue and FIG. 3b shows this inserted catheter with its balloon fully inflated and pressing against the tumor.
Figure 3A:
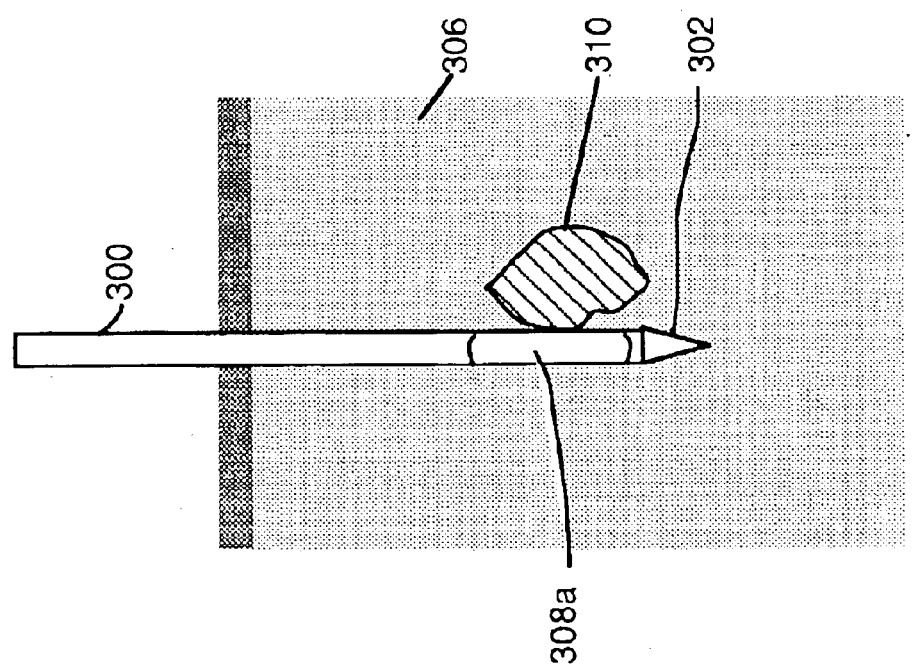

FIGS. 3a and 3b schematically illustrate the basic operation of either the generalized integrated-structure catheter-design embodiment shown in FIG. 1 or the preferred integrated-structure catheter-design embodiment shown in FIGS. 2a and 2b in treating a deep-seated tumor. In FIG. 3a, the sharp point 302 (insertion needle) of the integrated-structure catheter 300 is used to puncture skin 304 and the underlying sub-coetaneous tissue 306 and then position catheter so that its deflated balloon 308a is situated in proximity to tumor 310 of the patient being treated. As shown in FIG. 3b, balloon 308b is then inflated to press against tumor 310 (thereby deforming the shape of inflated balloon 308b), prior to tumor 310 being irradiated by microwave energy emitted from antenna 106 of FIG. 1 or antenna 214 of FIG. 2a. The following irradiation of tumor 310 preferably heats the tissue of tumor 310 in proximity to inflated balloon 308b to a temperature sufficient to (1) cause ablation and necrosis of proximate tumor cells, and (2) cause a "biological stent" to be formed (in a manner more fully described in the aforesaid prior-art U.S. Pat. No. 5,992,419). This results in a permanent cavity being formed within or in the immediate vicinity of tumor 310 after balloon 308b has been deflated and the catheter has been removed from the body of the patient.

Considering more particularly the operation of the preferred integrated-structure catheter-design embodiment shown in FIGS. 2a and 2b, retractable sheath 202 is maintained in it unretracted position with its distal end in contact with the proximate end of insertion needle 210 during the minimally-invasive procedure which is used to place the catheter in the position shown in FIG. 3a, after which retractable sheath 202 is retracted and the balloon 200 is fully inflated (as shown in FIG. 2a). More particularly, a cold gas (or, alternatively, a cold liquid) fluid transmitted in alternate ones of plastic tubes 218 (shown in FIG. 2b) to the interior of balloon 200 through opening 228 in plastic catheter body 206 (shown in FIG. 2a) and through opening 230 in plastic catheter body 206 and metal block 208 (shown in FIG. 2a) to inflate balloon 200 to its fully expanded condition shown in FIG. 2a. Preferably, the cold gas (or liquid) is supplied continuously under some pressure to the interior of balloon 200 through alternate ones of plastic tubes 218 (as indicated in FIG. 2a by arrow heads 232 pointing to the right), while the gas, now warmer, is continuously extracted from the interior of balloon 200 through opening 234 in plastic catheter body and through opening 236 in plastic catheter body 206 and metal block 208 through the remaining ones of plastic tubes 218 (as indicated by arrow heads 238 pointing to the left). At the same time, both metal block 208 and insertion needle 210 are cooled by initially cold liquid (indicated in FIG. 2a by arrow heads 240 pointing to the right) transmitted through inlet channel 222 (see FIG. 2b) and continuously flowing through toroidal hollow 242 (see FIG. 2a) in metal block 208 (where the liquid is warmed) and then (indicated in FIG. 2a by arrow heads 244 pointing to the left) extracted through outlet channel 224 (see FIG. 2b).

As mentioned above, central lumen 226 may be utilized to inject a substance, such as an immunological stimulating drug, into a deep-seated tumor being treated. More particularly, as part of the step of the catheter being removed from the patient's body, immunostimulants such as cytokines (e.g., F13L from Immunex Corporation), or heat shock proteins, etc. may be pumped into the aforesaid permanent cavity. Instead of immunostimulants, chemotherapeutic agents or bacterial vaccines such as Bacille Calmette Guerin (BCG) or mixed Bacterial Vaccine (MBV), etc. may be pumped into the aforesaid permanent cavity. These liquids slowly diffuse through the necrotic tissues formed by the aforesaid ablation procedure. In certain cases, the pumped liquid may include a gelatin base in which the therapeutic substance is dissolved. The presence of gelatin filling the cavity is effective in preventing the tendency, over time, of healed ablated sub-cutaneous tissue to close the cavity or, at least, diminish its size. Further, to prevent such pumped liquids from leaving the permanent cavity through the hole made by the catheter after the catheter has been removed from the patient's body, the hole may be plugged with collagen-based substances such as JEFLON (Upjohn Co.). In addition, it has been found that substances that cause bacterial or viral infections, such as for example living cultures of streptococci, may be introduced into a permanent cavity formed by ablation with a microwave balloon catheter of a solid malignant tumor. Further, because the aforesaid ablation process resulting from the heating of the irradiated tissue of tumor 310 in proximity to inflated balloon 308b may not by itself completely cause necrosis of all of the proximate tumor cells, necrosis of any tumor cell which survived the irradiation treatment may be effected by the introduction of a conventional chemotherapeutic substance into the permanent cavity formed by the ablation process.

Figure 4A:
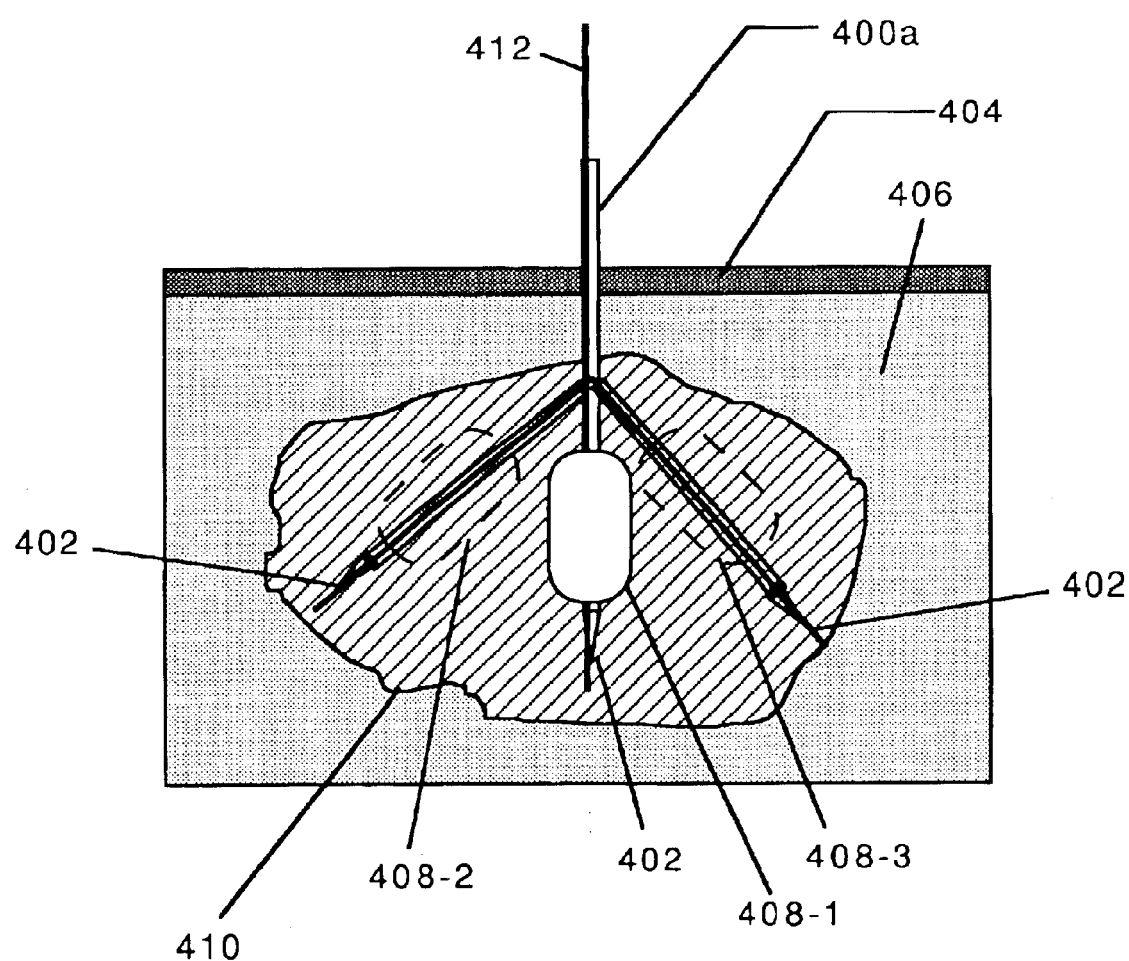
FIGS. 4a and 4b schematically show respective first and second modifications of the inflatable balloon catheter shown in FIGS. 3a and 3b suitable for treating a relatively large-volume tumor within deep-seated tissue.

FIG. 4a shows integrated-structure balloon catheter 400a for providing a first approach to treating a relatively large-volume deep-seated tumor 410. Catheter 400a, like the catheter of FIGS. 3a and 3b, includes sharp point 402 (insertion needle) for puncturing skin 404 and the underlying sub-coetaneous tissue 406 prior to entering the tissue of tumor 410. However, catheter 400a further includes guide wire 412 which permits the lower portion of catheter 400a including insertion needle 402 and balloon 408 to be bent to any of various selected angular positions. Thus, catheter 400a, with balloon 408 deflated, may be positioned in a first position within tumor 410, and then inflated (as indicated in FIG. 4a by the reference numeral 408-1) prior to being irradiated by microwave energy to form a first cavity within tumor 410 (as described above). Thereafter, catheter 400a, with balloon 408 deflated, may be partially withdrawn, and then, with the aid of guide wire 412, be successively repositioned in a second and third position within tumor 410, and then inflated (as indicated in FIG. 4a by the respective reference numerals 408-2 and 408-3) prior to being irradiated by microwave energy to form respective second and third cavities within tumor 410.

Figure 4B:
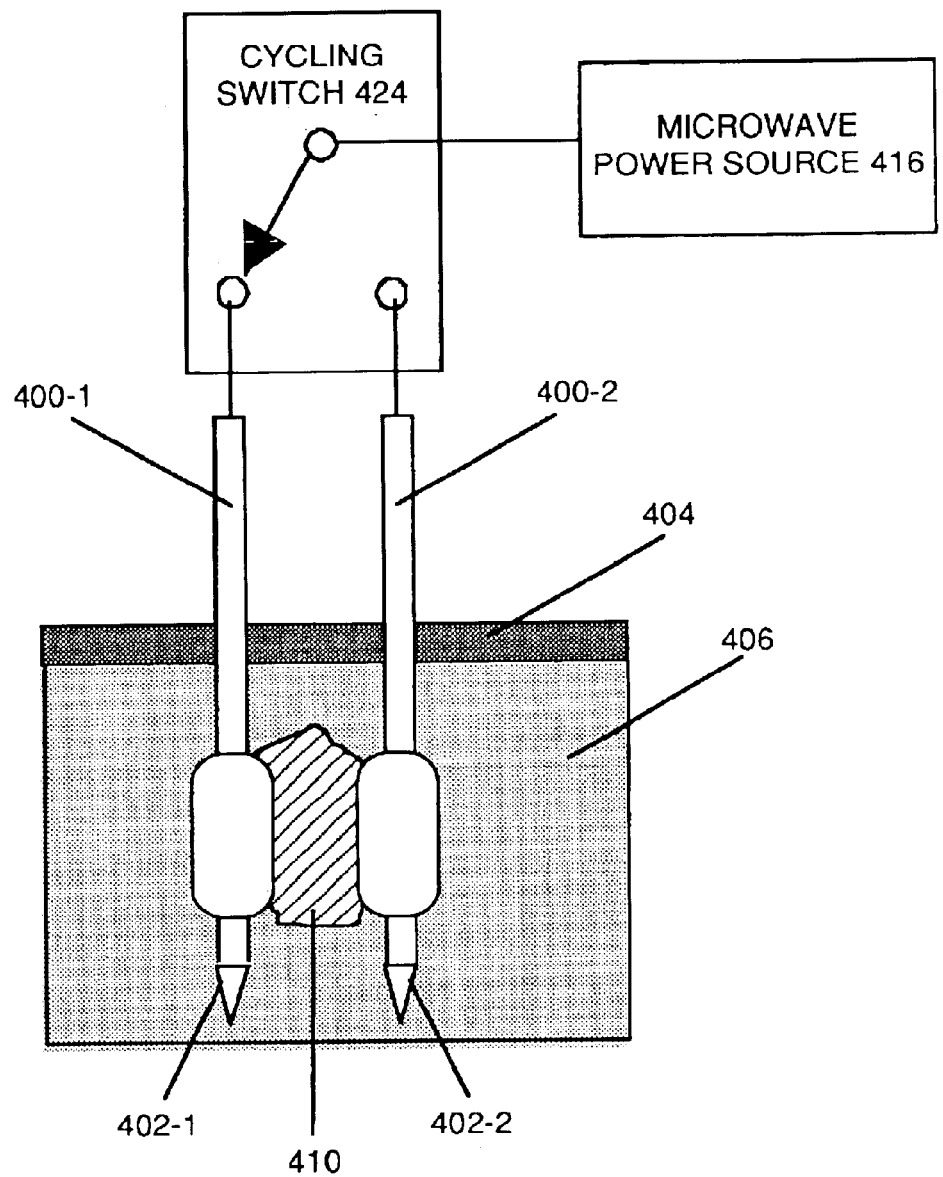

FIG. 4b shows two integrated-structure balloon catheters 400-1 and 400-2 for providing a second approach to treating a relatively large-volume deep-seated tumor 410. More specifically, sharp point 402-1 (insertion needle) of integrated-structure catheter 400-1 is used to puncture skin 404 and the underlying sub-coetaneous tissue 406 at a position that places balloon 408-1 in its deflated state in a first position within or in the vicinity of tumor 310 of the patient being treated and sharp point 402-2 (insertion needle) of integrated-structure catheter 400-2 is used to puncture skin 404 and the underlying sub-cutaneous tissue 406 at a position that places balloon 408-2 in its deflated state in a spatially spaced second position within or in the vicinity of tumor 310 of the patient being. Balloons 408-1 and 408-2 are then inflated (as shown in FIG. 4b). Cycling switch 414 is then used to apply microwave energy from single microwave power source 416 to each of catheters 400-1 and 400-2. Thereafter, balloons 408-1 and 408-2 are deflated and removed, thereby leaving a first cavity in tumor 410 in the neighborhood formerly occupied by inflated balloon 408-1 and a second cavity in tumor 410 in the neighborhood formerly occupied by inflated balloon 408-2.

Figure 5A:
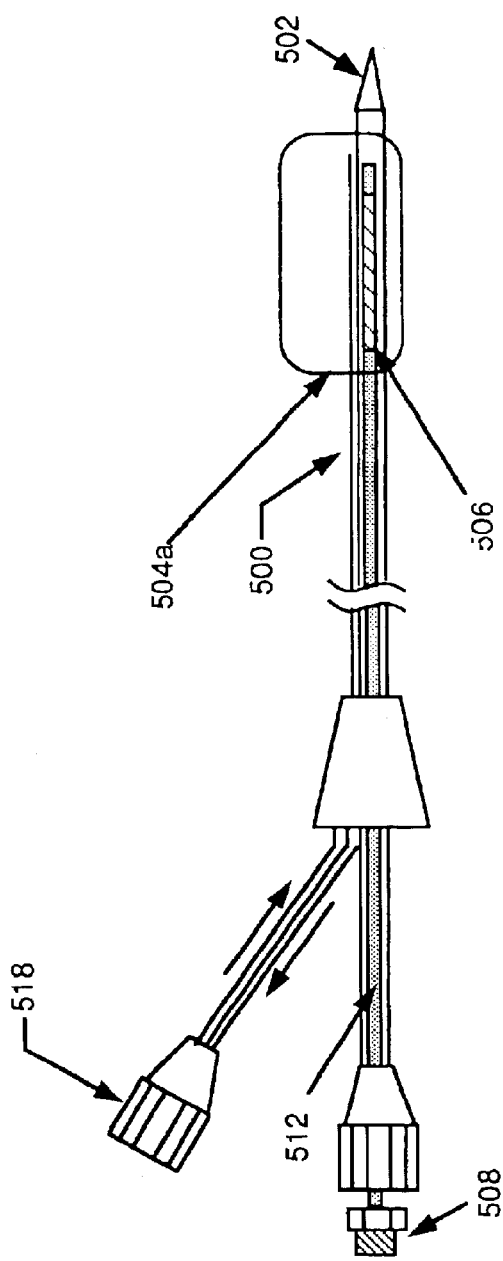
FIGS. 5a, 5b and 5c, respectively, comprise generalized diagrammatic showings of three different structural modifications of the inflatable balloon of the catheter design shown in FIG. 1.
Figure 5B:
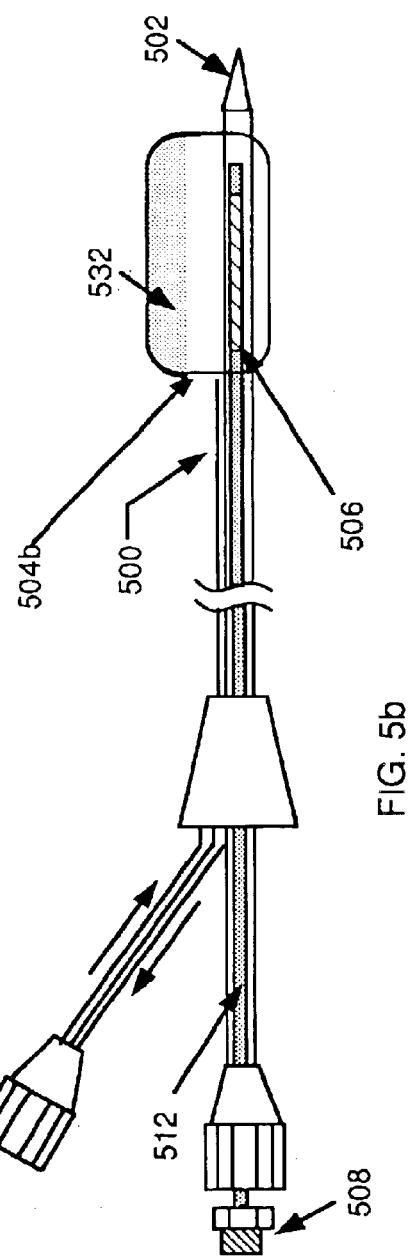
Figure 5C:
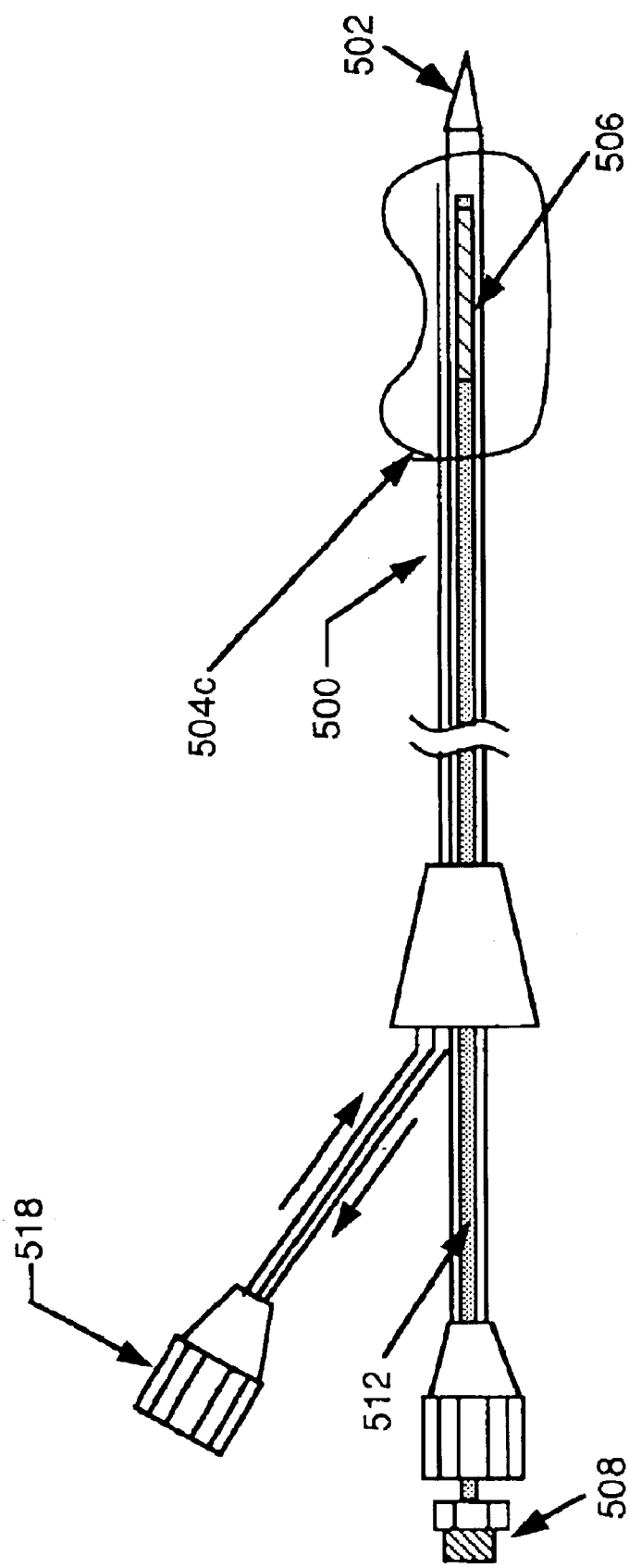

FIGS. 5a, 5b and 5c, respectively, comprise generalized diagrammatic showings of three different structural modifications of the inflatable balloon of the catheter design shown in FIG. 1. Except for its inflatable balloon, the structure of each of catheter 500 of FIGS. 5a, 5b and 5c is similar to catheter 100 of FIG. 1 except that a connector similar to connector 120 of FIG. 1 for providing a two-channel liquid flow for antenna and cable cooling has been omitted from the showing in each of FIGS. 5a, 5b and 5c. Thus, each of FIGS. 5a, 5b and 5c includes elements 502, 506, 508, 512 and 518 corresponding, respectively, with elements 102, 106, 108, 112 and 118 of FIG. 1.

The aforesaid U.S. Pat. No. 5,007,437 teaches that (1) a microwave antenna may be situated off axis, closer to diseased prostate tissue on one side of an inflated catheter balloon to be preferentially irradiated with respect to the irradiation of non-prostate tissue on the other side of the inflated catheter balloon and (2) a reflector may be utilized to further preferentially irradiate the prostate tissue. The first of these teachings is employed by the catheter design of FIG. 5a, in which inflated balloon 504a is oriented asymmetrically with the axis of antenna 506 being situated closer to the bottom than the top of inflated balloon 504a. Therefore, if tumor tissue were situated below inflated balloon 504a, it would be preferentially irradiated with respect to non-tumor tissue situated above inflated balloon 504a. The second of these teachings is employed by the catheter design of FIG. 5b, in which inflated balloon 504b is not only oriented asymmetrically with the axis of antenna 506 being situated closer to the bottom than the top of inflated balloon 504b, but the top portion of the plastic sheet material which comprises balloon 504b is covered with reflective metallic coating 532 that reflects microwave radiation incident thereon in a downward direction to increase the intensity of the preferential irradiation of the tumor tissue situated below inflated balloon 504b, while minimizing irradiation of the non-tumor tissue situated above inflated balloon 504b.

As known, the plastic sheet material employed in the fabrication of inflatable plastic toys may be may have a selected non-uniform, odd pattern shape which determines the identity of the particular toy design being fabricated (e.g., given animal, etc.). In a similar manner, the plastic sheet material which comprises balloon 504c may have a selected non-uniform, odd pattern shape which is chosen in accordance with the tumor tissue and/or the tissue in the vicinity of the tumor tissue of the patient being treated.

The deep-seated diseased tissue of a patient that may be treated by the use of the minimally-invasive balloon catheters shown in any of FIGS. 1, 2a and 2b, 5a, 5b or 5c described above is not limited to deep-seated tumors. For instance, The deep-seated diseased tissue of a patient may be a deep-seated cyst, rather than a tumor. In the case of a deep-seated cyst. In this case, antibiotics may be introduced into the cavity formed within or in the vicinity of the treated deep-seated cyst employing the operation described in detail above of any of the aforesaid catheters with its balloon in an inflated state.

Further, there are instances when one would want to fill the cavities with elastic materials such as silicones. This would be the case, for example, when one wants to increase the thickness of a herniated disk in the spinal column, In this case, a small cavity in the disc and then keep the cavity from collapsing by filling it with silicones.

Also, the News and Perspective article "Vanquishing Varicose Veins" appearing in *Health News/June* 2002 discloses a non-balloon catheter for use in applying either radio-frequency (RF) or laser energy in less-invasive treatments of varicose veins.

The use of a non-balloon catheter for applying either radio-frequency (RF) or laser energy in less-invasive treatments of varicose veins, is disclosed in the aforesaid News and Perspective article "Vanquishing Varicose Veins" appearing in *Health News/June* 2002, However, because of the fact that varicose veins are often gnarled and misshapen, this use inherently results in uneven heating of both the vein being treated and its immediately surrounding tissue, with the likelihood of producing undesired side effects in these tissues.

Each of the alternative integrated-structure balloon-catheter designs shown in FIGS. 6a and 6b, which use microwaves rather than RF, provides more uniform heating that minimizes the production of such undesired side effects.

Structurally, the balloon-catheter design diagrammatically shown in FIG. 6a comprises coaxial feedline 616a which runs through the length of plastic catheter body 600a with the outer conductor of coaxial feedline 616a terminating at the distal end of plastic body 600a with the remaining portion 613a (i.e., inner conductor and surrounding dielectric of coaxial feedline 616a) extending to and supporting sharp point (insertion needle) 602a. Spring antenna 606a, which is wound around the extended portion of the dielectric of coaxial feedline 616a, has its proximate end connected to the outer conductor and its distal end connected to insertion needle 602a. Taper-shaped balloon 604a has its proximate end attached to the outer surface of plastic body 600a and the proximate end of insertion needle 602a. Reference numeral 617a represents inflation tubes for supplying gas or liquid to the interior of balloon 604a to effect the inflation thereof and reference numeral 619a represents coolant tubes for supplying a coolant liquid to cool antenna 606a, should this be necessary. In those cases in which such cooling of antenna 606a proves to be unnecessary, coolant tubes 619a may be omitted.

In the operation of the balloon-catheter design diagrammatically shown in FIG. 6a, without any microwave power then being applied through coaxial feedline 616a to antenna 606a and with balloon 604a in its deflated state, insertion needle 602a is used to puncture the skin, enter a proximate end of a sub-cutaneous varicose vein of the patient, and then the entire catheter is pushed toward the distal end of that varicose vein. Thereafter, (1) balloon 604a is inflated, (2) microwave power is applied through coaxial feedline 616a to antenna 606a and (3) then, preferably while the catheter is partly rotated to twist and compress this varicose vein, the entire catheter is pulled back slowly toward the proximate end of that varicose vein. As the inflated balloon is pulled back, it stretches this varicose vein making the distance from antenna 606a to the portion of the vein then being heated by the radiated microwaves more uniform. This results in occluding and thereby closing each successive portion of the varicose vein, while substantially reducing the occurrence of undesirable side effects in the microwave-heated tissue, as the catheter, with its balloon in an inflated state, is pulled back.

The balloon-catheter design diagrammatically shown in FIG. 6b comprises elements 600b, 602b, 616b, 617b and 619b which structurally correspond, respectively, with elements 600a, 602a, 616a, 617a and 619a diagrammatically shown in above-described FIG. 6a. However, the balloon-catheter design diagrammatically shown in FIG. 6b structurally differs from that shown in FIG. 6a by (1) comprising end-fire antenna 606b (rather than spring antenna 606a) which may be energized by microwaves supplied to it by coaxial feedline 616b, (2) dielectric (preferably ceramic) support rod 615b extending from the distal end of end-fire antenna 606b to the proximate end of insertion needle 602b and (3) balloon 604b (which, unlike balloon 604a, is not tapered) having its proximate end attached to the outer surface of plastic body 600b and its distal end attached to an intermediate point along support rod 615b.

The operation of the balloon-catheter design diagrammatically shown in FIG. 6b is essentially the same as that described above for the operation of the balloon-catheter design diagrammatically shown in FIG. 6a.

All of the various balloon catheter designs of the present invention described above include a sharp-pointed insertion needle for use in puncturing the skin and entering underlying diseased tissue usually through intervening sub-cutaneous tissue. One of these above-described designs, shown in FIG. 5c, comprises a balloon that may have a selected non-uniform, odd pattern shape. However, the beneficial use of a balloon catheter design having such a selected non-uniform, odd pattern shape is not limited to its use in a balloon catheter design for use in puncturing the skin and entering underlying diseased tissue. It also has beneficial use in the structural modifications diagrammatically shown in FIGS. 7a and 7b of the prior-art balloon catheter design for treating prostate disease disclosed in the aforesaid is U.S. Pat. No. 5,007,437.

In the balloon catheter design shown in FIG. 7a for treating prostate disease, each of elements 700a, 706a, 708a, 716a and 718a correspond, respectively, to elements 100, 106, 108, 116 and 118 of the balloon catheter design shown in FIG. 1. However, balloon 705a is molded to have the non-uniform shape shown in FIG. 7a (where the width of a most proximate portion of inflated balloon 705a is substantially wider than the remaining portion of inflated balloon 705a) that performs the function when inflated of "pushing" the urethral sphincter tissue away from the prostate tissue being heated, rather than, like balloon 104, having the uniform cylindrical shape shown in FIG. 1. Balloon 705a is inflated through two-channel water/gas flow connector 718a. Further, as is conventional, the balloon catheter design shown in FIG. 7a for treating prostate disease includes a separate so-called "Foley" balloon 707a for insertion into the bladder of the patient, which, when inflated, holds the catheter in the proper position with respect to the prostate tissue to be treated. Balloon 707a is inflated through two-channel water/gas flow connector 721a.

In the balloon catheter design shown in FIG. 7b for treating prostate disease, the need for a separate "Foley" balloon, requiring a second two-channel water/gas flow connector for inflating it are both avoided by employing a single balloon 705b molded to have the non-uniform shape shown in FIG. 7b which, as shown, includes a bulb-shaped protuberance 709b projecting from the distal portion of single balloon 705b. Elements 700b 706b, 708b 716b and 718b of FIG. 7b correspond, respectively, with elements 700a 706a, 708a 716a and 718 of FIG. 7a.

While each of the above-described inflatable balloon catheter designs shown, respectively, in FIGS. 1, 2a and 2b, 3a and 3b, 4a, 4b, 5a, 5b and 5c employs a microwave radiating antenna as the preferred means for providing minimally-invasive heating of sub-cutaneous, deep-seated diseased tissue (e.g. a tumor or cyst) to a temperature sufficient to produce a permanent cavity (i.e., a "biological stent") within or in the vicinity of the deep-seated diseased tissue which is in contact the inflated balloon of the catheter, the use of a microwave radiating antenna for this purpose is not essential. There are many ways of providing this heating sufficient to produce the permanent cavity within or in the vicinity of the deep-seated diseased tissue which is in contact the inflated balloon of the catheter. Among these ways are (1) a radio-frequency (RF) radiating antenna (rather than a microwave radiating antenna), (2) means for producing a localized spatial field (e.g., a dielectric or induction field) emanating from a transducer which is not tuned to the energizing frequency supplied thereto), (3) radiation from a laser or an intense light-source, (4) an ultrasonic transducer (which requires that the balloon be inflated with a liquid (e.g., water), rather than a gas (e.g., air), or (5) even inflating the balloon with water that already has been preheated to a temperature sufficient to produce the permanent cavity within or in the vicinity of the deep-seated diseased tissue which is in contact the inflated balloon. The microwave, RF or ultrasonic radiated energy, as the case may be, can be either continuous-wave (CW) radiated energy or, alternatively, it may be pulsed radiated energy. Further, this radiated energy, if desired, can be frequency-modulated in order to avoid the unwanted generation of standing waves.

As described above, one of the main purposes of the present invention is to be able to inject a particular one of the above-described therapeutic substances into a permanent cavity situated within or near particular diseased sub-cutaneous tissue of a patient, wherein the permanent cavity has been produced by employing a minimally invasive procedure (preferably by the use of any of the above-described inflatable balloon catheter designs shown, respectively in FIGS. 1, 2a and 2b, 3a and 3b, 4a, 4b, 5a, 5b, 5c, 6a and 6b). However, the permanent cavity into which the particular ones of the above-described therapeutic substances is injected can be produced by some other type of minimally invasive procedure (e.g., arthroscopic surgery, for example).

What is claimed is:

1. In apparatus for use in providing a minimally-invasive treatment of diseased sub-cutaneous tissue of a patient, said apparatus comprising an integrated-structure inflatable-balloon catheter that includes a longitudinal structure having a sharply-pointed insertion needle at a distal end of said longitudinal structure and an inflatable balloon situated intermediate a proximate end and said distal end of said longitudinal structure which is attached to said longitudinal structure, whereby, with said inflatable balloon in a deflated state, said insertion needle may be used to puncture said patient's skin and underlying sub-cutaneous tissue and place said deflated balloon in proximity to said diseased sub-cutaneous tissue; means for inflating said inflatable balloon in said place to cause said inflated balloon to press against and thereby spatially deform said diseased sub-cutaneous tissue; and means, effective with said inflatable balloon remaining inflated in said place, for therapeutically heating said deformed diseased sub-cutaneous tissue; the improvement wherein said longitudinal structure comprises:

a flexible hollow plastic body having (1) first length and first width dimensions, (2) said insertion needle being attached to a distal end of said plastic body and (3) said inflatable balloon being attached to an exterior surface of said plastic body;

a rigid retractable sheath surrounding said plastic body, said sheath having a second length dimension which is substantially shorter than said first length dimension which permits said sheath to be moved between an unretracted state in which its distal end is situated in proximity to said insertion needle and a retracted state, and said sheath having a second width dimension which is sufficiently larger than said first width dimension to permit said inflatable balloon in a furled deflated state to be stored in a space between said outer surface of said plastic body and an interior surface of said sheath when said sheath is situated in said unretracted state and permit said inflatable balloon to be removed from said space and unfurl when said sheath is in said retracted state;

whereby said insertion needle may be first used to puncture said patient's skin and underlying sub-cutaneous tissue and place said deflated balloon in proximity to said diseased sub-cutaneous tissue with said retractable sheath in said unretracted state and then said retractable sheath may be retracted to thereby permit said deflated balloon to be inflated.

2. The apparatus defined in claim 1, wherein:

said insertion needle has a maximum width dimension which in size is at least that of said second width dimension.

3. The apparatus defined in claim 2, wherein:

said plastic body includes a tab at its proximate end which has a maximum width dimension which in size is at least that of said second width dimension.

4. The apparatus defined in claim 1, wherein said means for therapeutically heating said deformed diseased sub-cutaneous tissue comprises:

a microwave antenna situated within said plastic body at a longitudinal location in proximity to said inflatable balloon for radiating microwave energy supplied to said antenna; and means for supplying microwave energy to said antenna that includes a coaxial line situated within said plastic body that is adapted to be coupled to a microwave-energy source at the proximate end of said plastic body, and said coaxial line comprises an outer conductor attached to the interior surface of said plastic body and an inner conductor spaced from said outer conductor by dielectric material.

5. The apparatus defined in claim 4, wherein:

said insertion needle comprises metal material that is connected to the distal end of said inner conductor of said coaxial line; and said microwave antenna comprises a helical spring antenna having its proximate end connected to said outer conductor of said coaxial line and its distal end connected to said insertion needle.

6. The apparatus defined in claim 4, wherein:

said dielectric material comprises a plurality of contiguous longitudinal plastic tubes that are circumferentially-arranged about said inner conductor with all said tubes being in contact with both said outer and inner conductors to thereby provide support for said inner conductor and with a distal end of all said tubes being in contact with a proximate end of said insertion needle;

said plastic body and said plastic tubes having openings therethrough that are longitudinally-disposed in proximity to interior space of said inflatable balloon; and said means for inflating said inflatable balloon comprises means for supplying a fluid to a proximate end of at least a first subset of said tubes;

whereby said supplied fluid flows through said first subset of said tubes and enters the interior space of said inflatable balloon through said openings in said first subset of said tubes to thereby inflate said balloon.

7. The apparatus defined in claim 6, wherein:

said means for supplying said fluid comprises means for continuously pumping a gas through said first subset of said tubes and said openings in said first subset of said tubes to thereby inflate said balloon, while continuously extracting said gas from said inflated balloon through openings in a remaining subset of said tubes and then through said remaining subset of said tubes.

8. The apparatus defined in claim 7, wherein:
said first subset comprises alternate ones of said circumferentially-arranged plastic tubes and said remaining subset comprises remaining ones of said circumferentially-arranged plastic tubes.

9. The apparatus defined in claim 7, wherein:
said pumped gas is a cold gas; and
said insertion needle includes a first opening therethrough and said plastic body includes a first additional opening through which said pumped cold gas flowing in said first subset of said tubes may enter said inflatable balloon; and
said insertion needle includes a second opening therethrough and said plastic body includes a second additional opening through which said gas from said inflated balloon may be extracted through said remaining subset of said tubes and then through said remaining subset of said tubes.

10. The apparatus defined in claim 4, wherein:
said insertion needle is connected to the distal end of said inner conductor of said coaxial line and said inner conductor comprises a hollow tube having an interior surface that defines an interior space;
a longitudinal element attached to the interior surface of said inner conductor at each of two diametrically opposite points that runs the length of said inner conductor, whereby said element operates as a septum that divides said interior space into first and second separated channels;
said insertion needle comprises a toroidal hollow region connected to distal ends of both said first and second separated channels; and
said apparatus further comprises means for continuously pumping a coolant liquid into the proximate end of one of said first and second separated channels, whereby said coolant liquid (1) flows through said one of said first and second separated channels toward said toroidal hollow region, (2) then flows through said toroidal hollow region and (3) finally flows through the other of said first and second separated channels prior to being extracted at the proximate end of said second separated channels.

11. The apparatus defined in claim 10, wherein:
said longitudinal element together with said insertion needle defines a central lumen that runs the entire length thereof from the proximate end of said longitudinal element to a sharp point of said sharply-pointed insertion needle.

12. In apparatus for use in providing a minimally-invasive treatment of diseased sub-cutaneous tissue of a patient, said apparatus comprising an integrated-structure inflatable-balloon catheter that includes a longitudinal structure having a sharply-pointed insertion needle at a distal end of said longitudinal structure and an inflatable balloon situated intermediate a proximate end and said distal end of said longitudinal structure which is attached to said longitudinal structure, whereby, with said inflatable balloon in a deflated state, said insertion needle may be used to puncture said patient's skin and underlying sub-cutaneous tissue and place said deflated balloon in proximity to said diseased sub-cutaneous tissue; means for inflating said inflatable balloon in said place to cause said inflated balloon to press against and thereby spatially deform said diseased sub-cutaneous tissue; and means, effective with said inflatable balloon remaining inflated in said place, for therapeutically heating said deformed diseased sub-cutaneous tissue;, wherein said means for therapeutically heating said deformed diseased sub-cutaneous tissue comprises a microwave antenna situated at a longitudinal location of said longitudinal structure in proximity to said inflatable balloon for radiating microwave energy supplied to said antenna, and a microwave structure including a microwave power source, a microwave radiometer for temperature monitoring, and means including a microwave single pole-double throw (SPDT) switch for supplying microwave energy from said microwave power source to said microwave antenna only when said switch is in a first of said double-throw positions thereof and for supplying microwave energy sensed by said antenna, which is indicative of its current temperature, from said microwave antenna to said microwave radiometer only when said switch is in a second of said double-throw positions thereof; the improvement, wherein said means including a SPDT switch further includes:
a ratiometer for measuring power reflection to sense changes in treated tissue; and
a dual directional coupler for simultaneously supplying to said ratiometer (1) a first quantitative sample of the microwave power being forwarded to said antenna when said switch is in said first of said double-throw positions thereof and (2) a second quantitative sample of the microwave power being reflected back from said antenna when said switch is in said first of said double-throw positions thereof.

13. In apparatus for use in providing a minimally-invasive treatment of diseased sub-cutaneous tissue of a patient, said apparatus comprising an integrated-structure inflatable-balloon catheter that includes a longitudinal structure having a sharply-pointed insertion needle at a distal end of said longitudinal structure and an inflatable balloon situated intermediate a proximate end and said distal end of said longitudinal structure which is attached to said longitudinal structure, whereby, with said inflatable balloon in a deflated state, said insertion needle may be used to puncture said patient's skin and underlying sub-cutaneous tissue and place said deflated balloon in proximity to said diseased sub-cutaneous tissue; means for inflating said inflatable balloon in said place to cause said inflated balloon to press against and thereby spatially deform said diseased sub-cutaneous tissue; and means, effective with said inflatable balloon remaining inflated in said place, for therapeutically heating said deformed diseased sub-cutaneous tissue;, wherein said means for therapeutically heating said deformed diseased sub-cutaneous tissue comprises a microwave antenna situated at a longitudinal location of said longitudinal structure in proximity to said inflatable balloon for radiating microwave energy supplied to said antenna; the improvement wherein:
said microwave antenna is situated inside of said balloon;
a first longitudinal side of said balloon is transparent to microwave energy incident thereon and a second longitudinal side of said balloon situated opposite to said first longitudinal side is metallized to reflect microwave energy incident thereon back through said transparent first longitudinal side; and
said means for inflating said inflatable balloon in said place causes solely said first longitudinal side of said balloon to be pressed against and thereby spatially deform said diseased sub-cutaneous tissue.

14. The apparatus defined in claim 13, wherein:
said microwave antenna is asymmetrically situated inside of said balloon so as to be closer to said first longitudinal side of said balloon than to said second longitudinal side of said balloon.

15. In apparatus for use in providing a minimally-invasive treatment of diseased sub-cutaneous tissue of a patient, said apparatus comprising an integrated-structure inflatable-balloon catheter that includes a longitudinal structure having a sharply-pointed insertion needle at a distal end of said longitudinal structure and an inflatable balloon situated intermediate a proximate end and said distal end of said longitudinal structure which is attached to said longitudinal structure, whereby, with said inflatable balloon in a deflated state, said insertion needle may be used to puncture said patient's skin and underlying sub-cutaneous tissue and place said deflated balloon in proximity to said diseased sub-cutaneous tissue; means for inflating said inflatable balloon in said place to cause said inflated balloon to press against and thereby spatially deform said diseased sub-cutaneous tissue; and means, effective with said inflatable balloon remaining inflated in said place, for therapeutically heating said deformed diseased sub-cutaneous tissue;, wherein said means for therapeutically heating said deformed diseased sub-cutaneous tissue comprises a microwave antenna situated at a longitudinal location of said longitudinal structure in proximity to said inflatable balloon for radiating microwave energy supplied to said antenna; the improvement wherein:

said inflatable balloon is fabricated so that, when said balloon is inflated, said balloon has preformed therein a selected non-uniform, odd pattern shape.

16. In apparatus for use in providing a minimally-invasive treatment of diseased sub-cutaneous tissue of a patient, said apparatus comprising an integrated-structure inflatable-balloon catheter that includes a longitudinal structure having a sharply-pointed insertion needle at a distal end of said longitudinal structure and an inflatable balloon situated intermediate a proximate end and said distal end of said longitudinal structure which is attached to said longitudinal structure, whereby, with said inflatable balloon in a deflated state, said insertion needle may be used to puncture said patient's skin and underlying sub-cutaneous tissue and place said deflated balloon in proximity to said diseased sub-cutaneous tissue; means for inflating said inflatable balloon in said place to cause said inflated balloon to press against and thereby spatially deform said diseased sub-cutaneous tissue; and means, effective with said inflatable balloon remaining inflated in said place, for therapeutically heating said deformed diseased sub-cutaneous tissue; the improvement wherein said apparatus is for use in providing a minimally-invasive treatment of varicose vein tissue of a patient, wherein said insertion needle may be used to puncture said patient's skin and enter the interior of said varicose vein tissue and wherein:

said longitudinal structure together with said inflatable balloon in an inflated state forms (1) serially-connected relatively narrow-width and relatively wide-width longitudinal sections, wherein said narrow-width longitudinal section has its distal end attached to a proximate end of said insertion needle and said wide-width longitudinal section has its distal end attached to a proximate end of said narrow-width longitudinal section, and (2) a microwave antenna for radiating microwave energy supplied thereto toward that surrounding varicose vein tissue which is proximate to said narrow-width longitudinal section.

17. The apparatus defined in claim 16, wherein:
said inflatable balloon has a non-uniform shape in said inflated state comprising relatively narrow-width and relatively wide-width longitudinal portions with the proximate end of said relatively narrow-width portion being attached to said proximate end of said insertion needle;

said microwave antenna is a helical spring antenna situated solely within said narrow-width longitudinal portion of said inflatable balloon in said inflated state; and said longitudinal structure includes a coaxial feedline extending from the proximate end of said longitudinal structure to said helical spring antenna for supplying microwave energy thereto.

18. The apparatus defined in claim 16, wherein:

said microwave antenna is an end-fire antenna for radiating microwave energy supplied thereto toward said insertion needle;

said longitudinal structure comprises (1) means including a coaxial feedline within a housing that extends from a proximate end of said longitudinal structure to said end-fire antenna for supporting said end-fire antenna and supplying microwave energy to said end-fire antenna, and (2) a dielectric support rod extending from a distal end of said end-fire antenna to the proximate end of said insertion needle for supporting said insertion needle; and said inflatable balloon having a proximate end thereof attached to an exterior surface of said housing at a first point situated intermediate said proximate end of said longitudinal structure and said end-fire antenna and having a distal end thereof attached to said dielectric support rod at a second point situated intermediate said distal end of said end-fire antenna and said insertion needle, so that said end-fire antenna is situated entirely inside said inflatable balloon;

whereby, with said inflatable balloon inflated, said narrow-width longitudinal section comprises that portion of said dielectric support rod that extends between said second point and said insertion needle and said wide-width longitudinal section comprises that portion of said longitudinal structure that extends from said proximate end thereof to said second point of said dielectric support rod.

19. The apparatus defined in claim 18, wherein:
said dielectric support rod comprises ceramic material.

20. In apparatus for use in providing a minimally-invasive treatment of diseased sub-cutaneous tissue of a patient, said apparatus comprising an integrated-structure inflatable-balloon catheter that includes a longitudinal structure having a sharply-pointed insertion needle at a distal end of said longitudinal structure and an inflatable balloon situated intermediate a proximate end and said distal end of said longitudinal structure which is attached to said longitudinal structure, whereby, with said inflatable balloon in a deflated state, said insertion needle may be used to puncture said patient's skin and underlying sub-cutaneous tissue and place said deflated balloon in proximity to said diseased sub-cutaneous tissue; means for inflating said inflatable balloon in said place to cause said inflated balloon to press against and thereby spatially deform said diseased sub-cutaneous tissue; and means, effective with said inflatable balloon remaining inflated in said place, for therapeutically heating said deformed diseased sub-cutaneous tissue; the improvement wherein said apparatus is for use in providing a minimally-invasive treatment of relatively large-sized, deep-seated diseased sub-cutaneous tissue of a patient, wherein said apparatus further comprises:

a plurality of separate integrated-structure inflatable-balloon catheters each of which includes a longitudinal structure having (1) a sharply-pointed insertion needle at a distal end of said longitudinal structure, (2) an inflatable balloon situated intermediate a proximate end and said distal end of said longitudinal structure which is attached to said longitudinal structure and (3) a microwave antenna coupled to a distal end of a coaxial feedline for forwarding microwave energy supplied to a proximate end of said coaxial feedline to said microwave antenna;

whereby, in use, each of said plurality of separate integrated-structure inflatable-balloon catheters may be positioned to treat a different portion of said relatively large-sized, deep-seated diseased sub-cutaneous tissue with its inflated balloon pressing against and thereby spatially deforming that portion of said relatively large-sized, deep-seated diseased sub-cutaneous tissue with which it is positioned;

a microwave-energy source; and cyclically-operated means coupling said microwave-energy source to said proximate end of said coaxial feedline of said longitudinal structure of each of said plurality of said separate integrated-structure inflatable-balloon catheters in turn to thereby supply microwave energy to said microwave antenna of said longitudinal structure of each of said plurality of said separate integrated-structure inflatable-balloon catheters in turn.

21. The apparatus defined in claim 20, wherein:

said plurality of separate integrated-structure inflatable-balloon catheters consists of two separate integrated-structure inflatable-balloon catheters.

22. A method for use in providing treatment of diseased sub-cutaneous tissue of a patient, said method comprising the steps of:

(a) employing minimally-invasive means to heat cell tissue to a sufficiently high temperature to effect cell necrosis and form a "biological stent" in the creation of a permanent cavity which is contiguously situated with respect to said diseased sub-cutaneous tissue; and (b) introducing a therapeutic substance into said permanent cavity.

23. The method defined in claim 22, wherein:

said therapeutic substance introduced into said permanent cavity is dissolved in a gelatin base.

24. The method defined in claim 22, wherein:

said therapeutic substance comprises a selected one of immunostimulants (e.g. a cytokine or a heat shock protein), a chemotherapeutic agent, a bacterial vaccine (e.g. Bacille Calmette Guerin or mixed Bacterial Vaccine) or a bacterial or viral infectious agent, an antibiotic or an elastic material (e.g., a silicone).

25. The method defined in claim 22, wherein step (a) comprises the steps of:

(c) employing an integrated-structure inflatable-balloon catheter, wherein said catheter includes a longitudinal structure having a sharply-pointed insertion needle at a distal end of said longitudinal structure and an inflatable balloon in a deflated state situated intermediate a proximate end and said distal end of said longitudinal structure which is attached to said longitudinal structure, to puncture said patient's skin and underlying sub-cutaneous tissue with said pointed insertion needle and place said deflated balloon in proximity to said diseased sub-cutaneous tissue;

(d) inflating said inflatable balloon in said place to cause said inflated balloon to press against and thereby spatially deform said diseased sub-cutaneous tissue;

(e) while said inflatable balloon remains inflated in said place, heating said deformed diseased sub-cutaneous tissue to a temperature which is sufficient to cause a permanent deformation of said deformed diseased sub-cutaneous tissue;

(f) deflating said inflatable balloon; and (g) then withdrawing said catheter from said patient's underlying sub-cutaneous tissue and punctured skin, thereby causing said permanent deformation to result in said permanent cavity being created contiguously situated with respect to said diseased sub-cutaneous tissue.

26. The method defined in claim 25, wherein said longitudinal structure of said catheter includes a lumen extending the entire length of said longitudinal structure from the proximate end thereof through said insertion needle, and wherein said step (b) comprises the steps of:

(h) pumping said therapeutic substance in liquid form through said lumen into said permanent cavity while said catheter is being withdrawn, whereby the withdrawal of said catheter leaves a hole through said patient's skin and intervening tissue; and (i) plugging said hole with a collagen-based substance.

27. The method defined in claim 26, wherein:

said therapeutic substance in liquid form is dissolved in a gelatin base.

28. The method defined in claim 25, wherein:

said therapeutic substance comprises a selected one of immunostimulants (e.g. a cytokine or a heat shock protein), a chemotherapeutic agent, a bacterial vaccine (e.g. Bacille Calmette Guerin or mixed Bacterial Vaccine) or a bacterial or viral infectious agent, an antibiotic or an elastic material (e.g., a silicone).

29. The method defined in claim 26, wherein step (i) comprises:

(j) plugging said hole with JEFLON.

30. In apparatus comprising an inflatable-balloon catheter adapted to be inserted into the urethra of a male patient for treating prostate disease, wherein said catheter comprises an inflatable balloon and a microwave antenna situated inside of said inflatable balloon, whereby said catheter may be (1) inserted into said urethra while in a deflated state and positioned therein at a location at which both said balloon and said microwave antenna are in cooperative relationship with said patient's prostate tissue, (2) said balloon may be inflated to a given pressure for expanding the size of its cross-section, resulting in both said prostate tissue and that non-prostate tissue situated between said inflated balloon and said prostate tissue being squeezed and compressed, and (3) effecting the irradiation and consequent heating of said patient's prostate tissue with a given distribution of microwave field energy from said antenna when said catheter is fully inserted into said urethra and said balloon is inflated, the improvement in said apparatus; wherein:

said inflatable balloon is fabricated to have preformed therein a non-uniform, odd pattern shape which divides said inflatable balloon longitudinally into a relatively wide most proximate portion and a relatively narrow remaining portion, said microwave antenna being situated within said relatively narrow remaining portion and said relatively wide most proximate portion, after insertion and inflation of said balloon, being longitudinally located to cooperate with said patient's urethral sphincter tissue when said microwave antenna is longitudinally located to cooperate with said patient's prostate tissue;

whereby said patient's sphincter tissue is pushed away from said patient's prostate tissue being heated by said irradiation from said antenna.

31. In apparatus comprising an inflatable-balloon catheter adapted to be inserted into the urethra of a male patient for treating prostate disease, wherein said catheter comprises an inflatable balloon and a microwave antenna situated inside of said inflatable balloon, whereby said catheter may be (1) inserted into said urethra while in a deflated state and positioned therein at a location at which both said balloon and said microwave antenna are in cooperative relationship with said patient's prostate tissue, (2) said balloon may be inflated to a given pressure for expanding the size of its cross-section, resulting in both said prostate tissue and that non-prostate tissue situated between said inflated balloon and said prostate tissue being squeezed and compressed, and (3) effecting the irradiation and consequent heating of said patient's prostate tissue with a given distribution of microwave field energy from said antenna when said catheter is fully inserted into said urethra and said balloon is inflated, the improvement in said apparatus; wherein:

said balloon is fabricated to have preformed therein a bulb-shaped protuberance projecting from a distal portion thereof which is adapted to be inserted into said patient's bladder prior to said balloon, situated within said patient's bladder, being inflated to result in said bulb-shaped protuberance cooperating with the shape of said patient's bladder tissue to thereby maintain the position of said catheter within said patient's urethra;

whereby said inflatable balloon with its bulb-shaped protuberance constitutes a selected non-uniform, odd pattern shape that obviates the need for an additional independent "Foley" balloon for use in maintaining the position of said catheter within said patient's urethra.

* * * * *